(12) United States Patent
Lee et al.

(10) Patent No.: US 8,402,629 B2
(45) Date of Patent: Mar. 26, 2013

(54) METHOD OF MANUFACTURING HOLLOW MICRONEEDLE STRUCTURES

(75) Inventors: Dae Sik Lee, Daejeon (KR); Yong Sun Yoon, Daejeon (KR); Moon Youn Jung, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 745 days.

(21) Appl. No.: 12/635,480

(22) Filed: Dec. 10, 2009

(65) Prior Publication Data

US 2011/0005669 A1    Jan. 13, 2011

(30) Foreign Application Priority Data

Jul. 7, 2009    (KR) .................. 10-2009-0061620

(51) Int. Cl.
*B23P 25/00* (2006.01)
*B22D 11/126* (2006.01)
*A61M 5/32* (2006.01)
*B05D 3/12* (2006.01)

(52) U.S. Cl. ......... 29/458; 29/527.1; 604/272; 604/264; 427/2.28; 427/289

(58) Field of Classification Search .............. 29/458, 29/527.1; 427/2.28, 230, 402, 2.1; 604/264, 604/272

See application file for complete search history.

(56) References Cited

U.S. PATENT DOCUMENTS

| | | | |
|---|---|---|---|
| 4,430,358 A * | 2/1984 | Wada | 427/2.28 |
| 6,334,856 B1 * | 1/2002 | Allen et al. | 604/191 |
| 6,511,463 B1 * | 1/2003 | Wood et al. | 604/272 |
| 7,332,197 B2 | 2/2008 | Wood et al. | |
| 7,785,459 B2 * | 8/2010 | Raju et al. | 205/73 |
| 7,789,733 B2 * | 9/2010 | Sugimura et al. | 451/58 |
| 2002/0138049 A1 | 9/2002 | Allen et al. | |
| 2003/0009113 A1 * | 1/2003 | Olson | 600/573 |
| 2003/0057249 A1 | 3/2003 | Orikasa et al. | |

(Continued)

FOREIGN PATENT DOCUMENTS

| | | |
|---|---|---|
| JP | 2005-021677 | 1/2005 |
| KR | 10-1989-0009493 A | 8/1989 |

(Continued)

OTHER PUBLICATIONS

Patrick Griss et al., "Side-Opened Out-of-Plane Microneedles for Microfluidic Transdermal Liquid Transfer," Journal of Microelectromechanical Systems, Jun. 2003, pp. 296-301, vol. 12, No. 3.

*Primary Examiner* — Timothy Meeks
*Assistant Examiner* — Cachet Sellman

(57) ABSTRACT

Provided is a method of manufacturing a hollow microneedle structure. The method includes coating a hollow core having a predetermined section and being long in a lengthwise direction with a coating solution, and solidifying the coating solution to form a coating layer, depositing a metal seed layer on the coating layer, plating the seed metal layer with a metal to form a plated layer, cutting the hollow core having the plated layer at an inclination angle with respect to the lengthwise direction for form a surface inclination, and removing the hollow core and the coating layer to form a hollow microneedle structure. Thus, the hollow microneedle structure can be manufactured to have such diameter, length, hardness, and inclination angle as to minimize pain. By use of the hollow core, the microneedle structure can have vertical microneedles with a uniform inner diameter.

9 Claims, 6 Drawing Sheets

U.S. PATENT DOCUMENTS

| | | | |
|---|---|---|---|
| 2003/0089414 A1 | 5/2003 | Ooyauchi et al. | |
| 2005/0209565 A1* | 9/2005 | Yuzhakov et al. | 604/173 |
| 2006/0025717 A1 | 2/2006 | Zimmermann et al. | |
| 2006/0084942 A1* | 4/2006 | Kim et al. | 604/890.1 |
| 2006/0202385 A1* | 9/2006 | Xu et al. | 264/219 |
| 2007/0233016 A1* | 10/2007 | Kuo et al. | 604/272 |

FOREIGN PATENT DOCUMENTS

| | | |
|---|---|---|
| KR | 10-2001-0011936 A | 2/2001 |
| KR | 10-2003-0036056 A | 5/2003 |
| KR | 100781702 B1 | 11/2007 |
| KR | 10-2003-0025790 A | 3/2009 |
| WO | WO 2005/049107 A2 | 6/2005 |

* cited by examiner

201a

201b

201c

202a

202b

202c

METHOD OF MANUFACTURING HOLLOW MICRONEEDLE STRUCTURES

CROSS-REFERENCE TO RELATED APPLICATION

This application claims priority to and the benefit of Korean Patent Application No. 10-2009-0061620, filed Jul. 7, 2009, the disclosure of which is incorporated herein by reference in its entirety.

BACKGROUND

1. Field of the Invention

The present invention relates to a method of manufacturing hollow microneedles, and more specifically, to a method of manufacturing hollow microneedles in which a hollow is formed using microthreads.

2. Discussion of Related Art

In the field of bio-microelectromechanical systems (bio-MEMS) technology, samples may need to be pretreated in order to enable early detection and chemical analysis for diseases on small chips. This requires collecting blood while minimizing pain. Accordingly, an essential component called a microneedle is required.

In general, needles are variously utilized in hospitals. For example, the needles are used to collect biomaterials, such as blood, in order to detect diseases, inject drugs into the living body, or perform cosmetic treatment of the skin.

Thus, a vast amount of research has been conducted on developing various applicable bioanalysis chips all over the world.

However, conventional needles used to collect biomaterials, such as blood, are practically problematic because they may cause pain during use and inflict external injuries.

Therefore, the demand for new microneedles capable of collecting blood while minimizing pain has increased globally.

Conventionally, probe-type microspikes, solid microneedles, and hollow microneedles have been proposed.

Compared to conventional needles, microneedles are capable of minimizing pain during penetration into the skin without leaving external injuries.

In order to minimize pain while penetrating the skin, a top diameter of a needle is important in providing more opportunities to avoid pain spots on the skin. Above all, a microneedle should penetrate a stratum corneum and a epidermis having a thickness of about 10 to 20 μm and 100 μm, respectively. To do this, the microneedle needs to have a certain degree of physical strength.

In addition, a microneedle should have an appropriate length as to reach as far as a capillary vessel in order to effectively collect blood or transmit medicine.

In consideration of all the above-described points, a technique of manufacturing a solid silicon microneedle having an out-of-plane shape using silicon MEMS technology has been introduced. However, this technique requires an additional etching process to provide a hollow needle shape, or does not satisfy a required needle length.

Meanwhile, although a microneedle having a sufficient length has recently been proposed using a drawing method, the proposed microneedle neither ensures verticality and uniformity nor realizes process simplification.

SUMMARY OF THE INVENTION

The present invention is directed to a method of manufacturing a hollow microneedle structure, which can ensure such a hardness as to penetrate the skin and such a length as to reach a capillary vessel. Also, the method of manufacturing the hollow microneedle structure may provide a microneedle structure having vertical needles with a uniform inner diameter using a simple process.

One aspect of the present invention provides a method of manufacturing a microneedle structure. The method includes: coating a hollow core having a predetermined section and being long in a lengthwise direction with a coating solution, and solidifying the coating solution to form a coating layer; depositing a metal seed layer on the coating layer; plating the seed metal layer with a metal to form a plated layer; cutting the hollow core having the plated layer at an inclination angle with respect to the lengthwise direction to form a surface inclination; and removing the hollow core and the coating layer to form a hollow.

The hollow core may be a microthread.

The microneedle structure may have an outer diameter of about 40 to 200 μm and an inner diameter of about 10 to 150 μm.

The microneedle structure may have an effective length of about 0.5 to 5 mm.

The method may further include: providing a substrate having an opening; arranging the microneedle structure through the opening; and adhering the microneedle structure to the substrate.

The method may further include chemically treating the hollow of the microneedle structure to prevent hardening of a biomaterial.

The coating solution may be a photoresist polymer.

The coating layer may have a circular or elliptical sectional shape.

The section of the hollow core may have a circular shape, a polygonal shape, or a stellar shape.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF EMBODIMENTS

Figure 1:
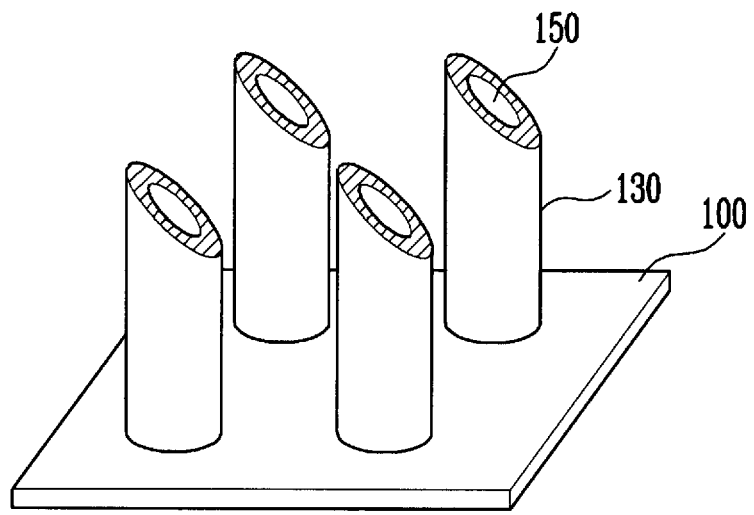
FIG. 1 is a construction diagram of a microneedle structure according to an exemplary embodiment of the present invention.

The present invention will be described more fully hereinafter with reference to the accompanying drawings, in which exemplary embodiments of the invention are shown. This invention may, however, be embodied in many different forms and should not be construed as being limited to the embodiments set forth herein. Rather, these embodiments are provided so that this disclosure is thorough and complete and fully conveys the concept of the invention to those skilled in the art. In the drawings, portions irrelevant to a description of the invention are omitted for brevity, and like numbers refer to like elements throughout.

As used herein, the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, a microneedle structure according to an exemplary embodiment of the present invention will be described with reference to FIG. 1.

Referring to FIG. 1, a microneedle structure manufactured according to an exemplary embodiment of the present invention may include a plurality of cylindrical microneedles 130. Each of the cylindrical microneedles 130 may include a hollow 150 formed in the center thereof.

That is, the plurality of microneedles 130 may be vertically formed on a single substrate 100, and an end tip of each of the microneedles 130 may be inclined.

Each of the microneedles 130, which may be obtained by plating a metal seed with nickel, may have a hollow 150 with a very small diameter of, for example, 0.01-200 µm or less, and satisfy an outer diameter of about 40 to 200 µm, an inner diameter of about 10 to 150 µm, and an effective length of about 0.5 to 5 mm.

The microneedles 130 may be formed using a hollow core, such as a microthread, to obtain the hollow 150 with the very small diameter.

Hereinafter, a method of manufacturing the microneedle structure of FIG. 1 will be described with reference to FIGS. 2A through 5B.

Figure 2A:
FIGS. 2A through 2F are cross-sectional views illustrating a method of manufacturing the microneedle structure of FIG. 1.
Figure 2B:
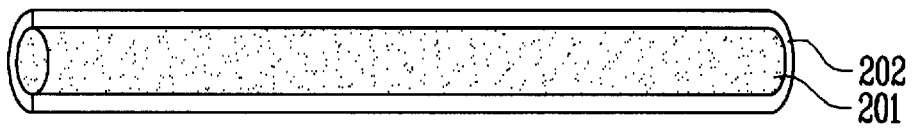
Figure 2C:
Figure 2D:
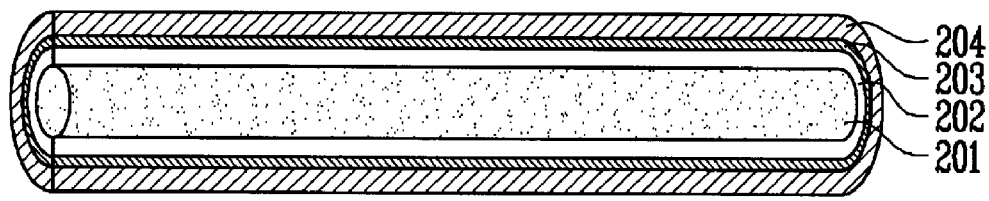
Figure 2E:
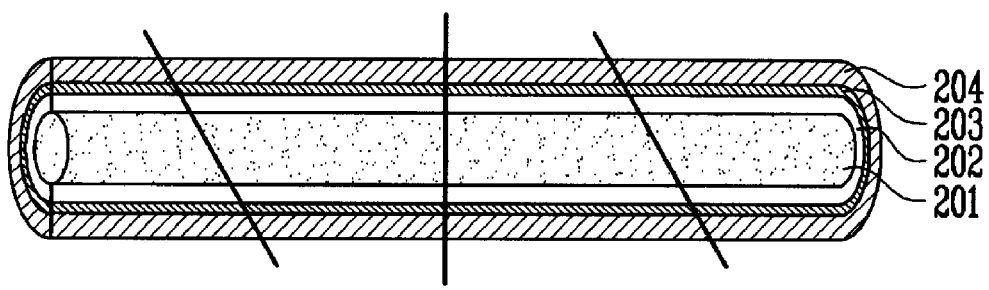
Figure 2F:
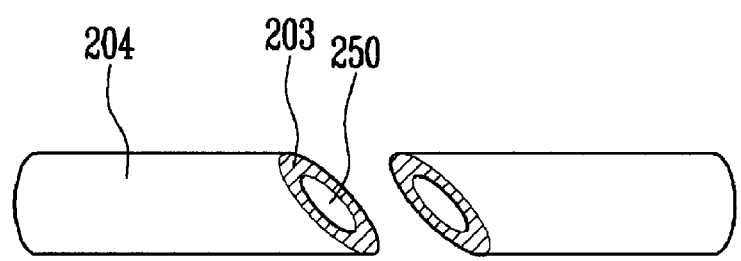
Figure 3A:
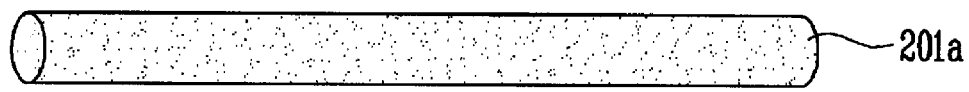
FIGS. 3A and 3B are diagrams showing the shape of a hollow core of FIG. 2A.
Figure 3A:
Figure 3A:
Figure 3B:
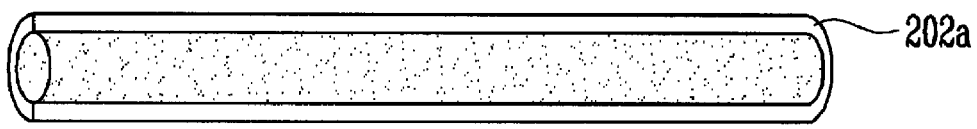
Figure 3B:
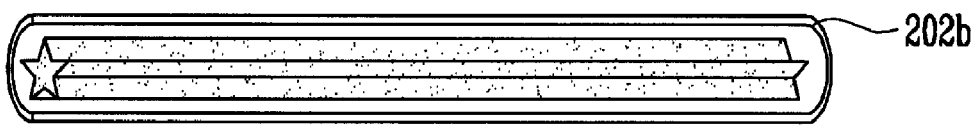
Figure 3B:
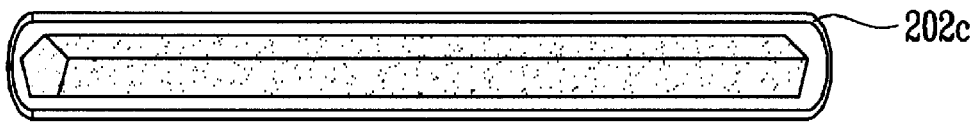
Figure 4A:
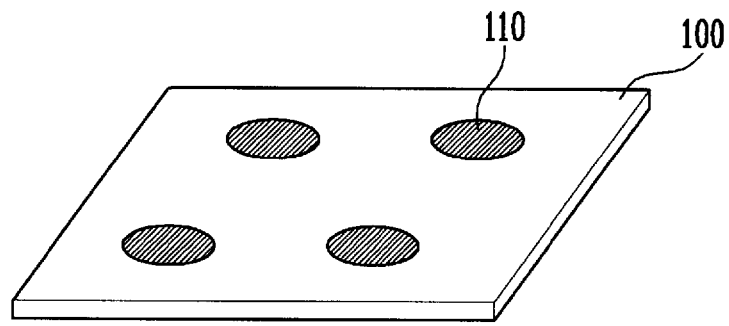
FIGS. 4A through 4C are diagrams illustrating subsequent processes performed on the resultant structure of FIG. 2F.
Figure 4B:
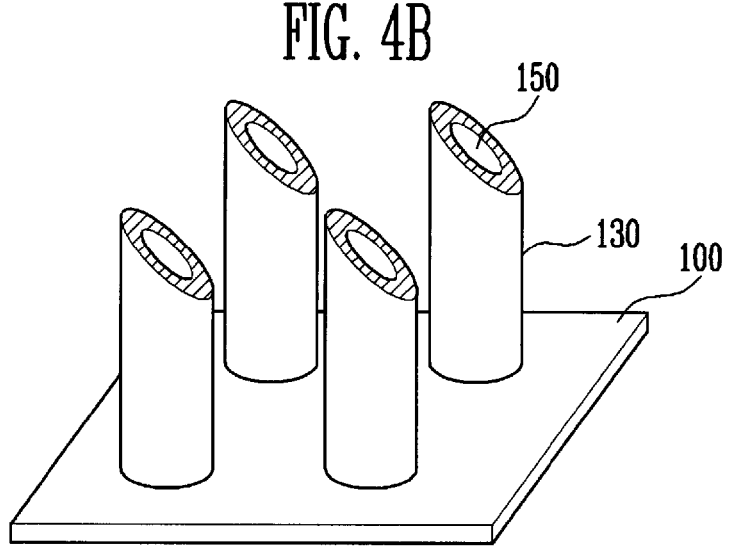
Figure 4C:
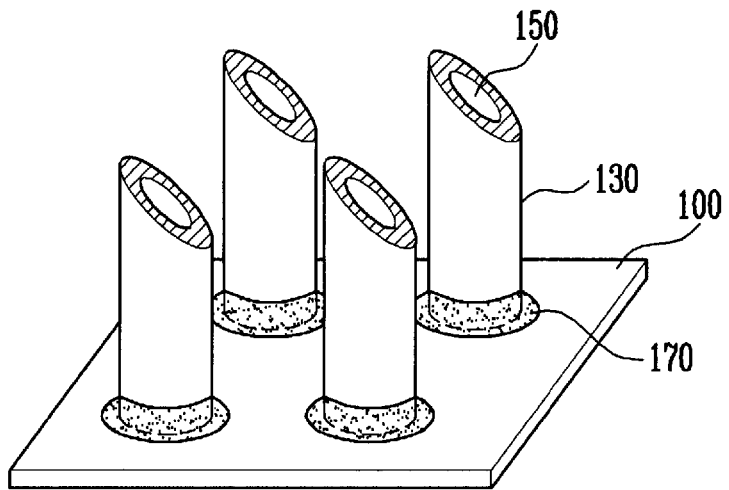
Figure 5A:
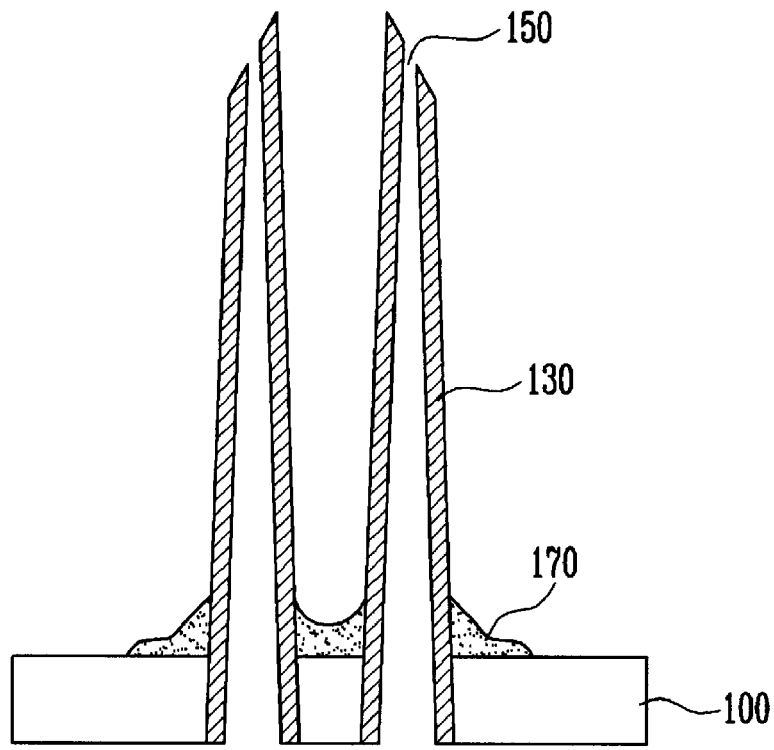
FIGS. 5A and 5B are construction diagrams of a microneedle structure obtained using the processes of FIGS. 4A through 4C.
Figure 5B:
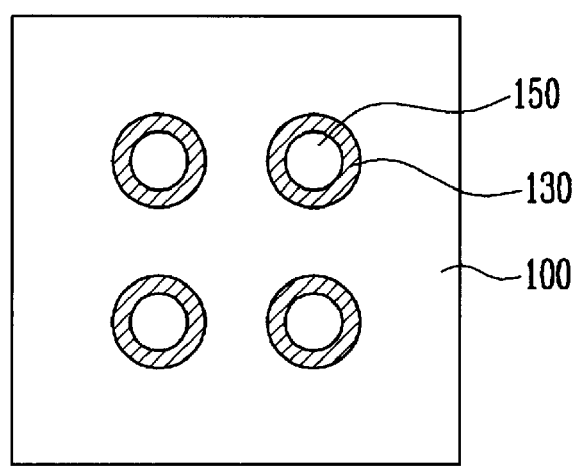

FIGS. 2A through 2F are cross-sectional views illustrating a method of manufacturing the microneedle structure of FIG. 1, FIGS. 3A and 3B are diagrams showing the shape of a hollow core of FIG. 2A, FIGS. 4A through 4C are diagrams illustrating subsequent processes performed on the resultant structure of FIG. 2F, and FIGS. 5A and 5B are construction diagrams of a microneedle structure obtained using the processes of FIGS. 4A through 4C.

To begin with, referring to FIG. 2A, a hollow core 201 may be prepared.

The hollow core 201 may be a microthread and have one of various sectional shapes as shown in FIG. 3A.

The hollow core 201 may have a wide range of diameters, that is, a diameter of about 0.01 to 200 µm. For example, the hollow core 201 may have a circular sectional shape 201a, a polygonal sectional shape 201b, or a stellar sectional shape 201c.

In this case, the inner diameter of the microneedle 130 may depend on the diameter of the hollow core 201.

Referring to FIG. 2B, the hollow core 201 may be coated with a photoresist containing silicon oxide, such as water glass, or a typical photoresist polymer.

When the hollow core 201 is coated with a photoresist material, a coating layer 202 may have an elliptical or circular sectional shape 202a, 202b, or 202c irrespective of the sectional shape of the hollow core 201 as shown in FIG. 3B and a planar surface.

Specifically, the hollow core 201 may be coated with water glass using a dipping process, thereby forming the circular coating layer 202. Thereafter, the coating layer 202 may be cured using ultraviolet (UV) rays or heat.

In this case, water glass or a photoresist polymer may be cured by UV rays or heat irrespective of the kind thereof. After a metal plating process, the water glass or photoresist polymer should be capable of being removed using an etchant.

Referring to FIG. 2C, a seed layer 203 may be formed on the coating layer 202.

The seed layer 203 may be formed by depositing a metal, such as titanium (Ti) or chrome (Cr), using one of various vacuum evaporation methods, such as an electronic beam (e-beam) evaporation process, a sputtering process, a chemical vapor deposition (CVD) process, or an atomic layer deposition (ALD) process by means of an e-beam vacuum evaporator, a heat vacuum evaporator, or a sputtering apparatus. The seed layer 203 may be electroplated with a metal, such as nickel (Ni) or gold (Au), thereby forming a plated layer 204 of FIG. 2D. In this case, the thickness of the plated layer 204 may be variously determined according to the hardness of a needle by controlling temperature, current density, and plating speed. For example, the plated layer 204 may be formed to a thickness of about 5 to 200 µm.

In this case, referring to FIG. 2E, the resultant structure having the plated layer 204 may be inclined using a cutting or sawing process in order to increase the sectional area of the needle.

Specifically, the resultant structure having the plated layer 204 may be cut at one of various inclination angles, thereby manufacturing the microneedle 130, such as a barbell-shaped microneedle, with one of various effective sectional areas. By increasing the effective area of the microneedle 130, the amount of a biomaterial collected may be also increased. In this case, the resultant structure having the plated layer 204 may be cut using a polishing process at an inclination angle of about 20 to 80 degrees with respect to a lengthwise direction of the hollow core 201. Alternatively, a conventional laser cutting process or mechanical cutting process may be performed without a slurry filling process.

Finally, referring to FIG. 2F, the hollow core 201 and the coating layer 202 of the inclined resultant structure may be simultaneously removed, thereby manufacturing a microneedle having a hollow 250.

The hollow core 201 and the coating layer 202 may be simultaneously removed using an appropriate etchant, such as hydrogen fluoride (HF). Also, the hollow core 201 may be removed by means of an ashing apparatus using plasma or a physical process.

Meanwhile, as shown in FIGS. 4A through 4C, a microneedle structure in which the microneedle 130 of FIG. 2F is vertically arranged on the substrate 100 may be manufactured.

Referring to FIG. 4A, a required number of openings 110, each of which has a diameter corresponding to the outer diameter of the microneedle 130, may be formed in the substrate 100.

Next, referring to FIG. 4B, the microneedle 130 having an inclined surface and the hollow 150 as shown in FIG. 2F may be vertically arranged on the substrate 100 through the opening 110 formed in the substrate 100. In this case, the effective length of the microneedle structure may be determined by controlling the penetrated length of the microneedle 130.

Finally, referring to FIG. 4C, an adhesive 170 may be injected into an interface between the substrate 100 and the microneedle 130 to fix the microneedle 130, thereby completing the manufacture of a 2×2 microneedle structure.

Referring to FIGS. 5A and 5B, a 2×2 microneedle structure may be formed by regularly arranging a plurality of microneedles 130, each of which has a thin, long section.

Meanwhile, a chemical treatment using an anticoagulant, such as EDTA or heparin, may be performed on an inner wall of the microneedle 130 having the hollow 150 to prevent the hardening of a biomaterial, such as blood. Alternatively, the inner wall of the microneedle 130 having the hollow 150 may be reformed using a plasma treatment such that the microneedle 130 has a hydrophilic inner surface. Furthermore, a biofriendly lubricant may be further applied to facilitate penetration of the microneedle through the skin.

Figure 6:
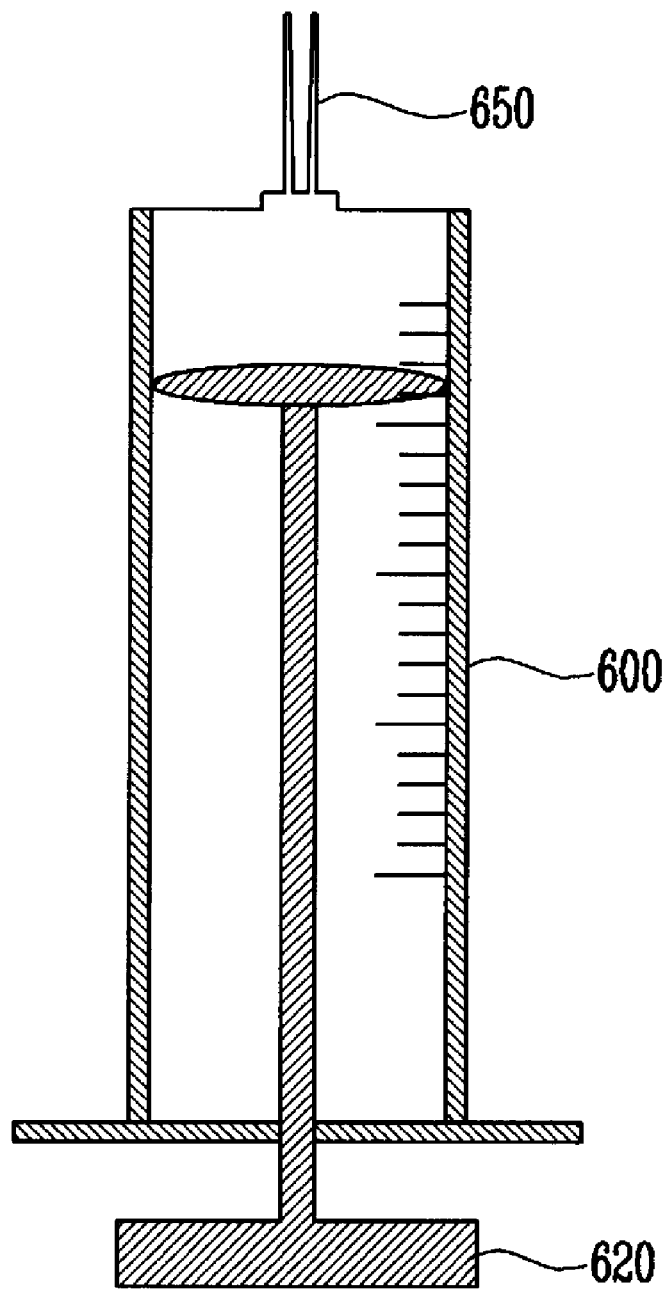
FIG. 6 is a construction diagram of an application example of the microneedle structure of FIG. 1.

FIG. 6 is a construction diagram of an application example of the microneedle structure of FIG. 1.

Referring to FIG. 6, a hollow microneedle structure 650 may be typically mounted on an injector. Specifically, a typical injector may include an injector main body 600 and a piston 620. The hollow microneedle structure 650 according to an exemplary embodiment of the present invention may be assembled on top of the injector main body 600 so that a biomaterial can be collected or a medicine may be injected.

According to the exemplary embodiments of the present invention, a hollow microneedle structure can be manufactured to have such a diameter, length, hardness, and inclination angle as to minimize pain. By use of hollow cores, the hollow microneedle structure can have vertical microneedles with a uniform inner diameter. Thus, the hollow microneedle structure can be combined with an apparatus for detecting a biomaterial or injecting cosmetic substances or medicine, and variously applied.

In the drawings and specification, there have been disclosed typical exemplary embodiments of the invention and, although specific terms are employed, they are used in a generic and descriptive sense only and not for purposes of limitation. As for the scope of the invention, it is to be set forth in the following claims. Therefore, it will be understood by those of ordinary skill in the art that various changes in form and details may be made therein without departing from the spirit and scope of the present invention as defined by the following claims.

What is claimed is:

1. A method of manufacturing a microneedle structure, comprising:
    coating a hollow core having a predetermined section and being long in a lengthwise direction with a coating solution, and solidifying the coating solution to form a coating layer;
    depositing a metal seed layer on the coating layer;
    plating the seed layer with a metal to form a plated layer;
    cutting the hollow core having the plated layer at an inclination angle with respect to the lengthwise direction to form a surface inclination; and
    removing the hollow core and the coating layer to form a hollow microneedle structure.

2. The method of claim 1, wherein the hollow core is a microthread.

3. The method of claim 2, wherein the microneedle structure has an outer diameter of about 40 to 200 µm and an inner diameter of about 10 to 150 µm.

4. The method of claim 2, wherein the microneedle structure has an effective length of about 0.5 to 5 mm.

5. The method of claim 1, further comprising:
    providing a substrate having an opening;
    arranging the microneedle structure through the opening; and
    adhering the microneedle structure to the substrate.

6. The method of claim 1, further comprising chemically treating the hollow of the microneedle structure to prevent hardening of a biomaterial.

7. The method of claim 1, wherein the coating solution is a photoresist polymer.

8. The method of claim 7, wherein the coating layer has a circular or elliptical sectional shape.

9. The method of claim 1, wherein the section of the hollow core has a circular shape, a polygonal shape, or a stellar shape.

* * * * *